United States Patent
Angeletakis et al.

(10) Patent No.: US 6,649,146 B2
(45) Date of Patent: *Nov. 18, 2003

(54) DENTAL IMPRESSION MATERIAL UTILIZING RUTHENIUM METATHESIS CATALYST

(75) Inventors: Christos Angeletakis, Orange, CA (US); Mingfei Chen, Monterey Park, CA (US)

(73) Assignee: Kerr Corporation, Orange, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 10/010,777

(22) Filed: Dec. 6, 2001

(65) Prior Publication Data

US 2002/0071813 A1 Jun. 13, 2002

Related U.S. Application Data

(63) Continuation-in-part of application No. 09/690,236, filed on Oct. 17, 2000, now Pat. No. 6,455,029.

(51) Int. Cl.[7] .................. A61K 7/16; C08L 83/05; C08L 5/24; C08L 3/34
(52) U.S. Cl. .................. 424/49; 523/107; 523/109; 524/264; 524/448
(58) Field of Search .................. 424/49; 523/107, 523/109, 264, 448

(56) References Cited

U.S. PATENT DOCUMENTS

| | | | |
|---|---|---|---|
| 5,831,108 A | 11/1998 | Grubbs et al. | 556/21 |
| 6,121,362 A | 9/2000 | Wanek et al. | 524/448 |
| 6,455,029 B1 * | 9/2002 | Angeletakis et al. | 424/49 |

FOREIGN PATENT DOCUMENTS

EP 0796607 9/1997 ............ A61K/6/00

OTHER PUBLICATIONS

Kim et al., *Surface–Initiated Ring–Opening Metathesis Polymerization on Si/SiO$_2$*, Macromolecules 2000, 33(8), 2793–2795.

* cited by examiner

*Primary Examiner*—Zohreh Fay
*Assistant Examiner*—Brian-Yong S. Kwon
(74) *Attorney, Agent, or Firm*—Wood, Herron & Evans, LLP

(57) ABSTRACT

A composition for use as a dental impression material including a polymerizable resin consisting of oligomers or polymers functionalized with groups curable by ring opening metathesis polymerization. These oligomers or polymers are end-capped and/or tethered with said functional groups. The composition also includes a ruthenium carbene complex catalyst, whereby the catalyst initiates ring-opening metathesis polymerization of the composition. The invention includes a paste/paste system in which a base paste includes the polymerizable oligomer or polymer and an inorganic dental filler system and in which a catalyst paste includes the catalyst dissolved in an inert solvent and an inorganic dental filler system. The oligomer or polymer may be, for example, one or a combination of a telechelic polydimethylsiloxane end-capped with norbornenyl groups, a polydimethylsiloxane tethered and end-capped with norbornenyl groups, a tri-functional polydimethylsiloxane end-capped with norbornenyl groups, or a quadri-functional polydimethylsiloxane end-capped with norbornenyl groups. The catalyst may be, for example, a ruthenium carbene complex with a ligand having a basicity higher than tricyclohexylphosphine. The composition of the present invention exhibits reduced sensitivity to sulfur impurities.

56 Claims, No Drawings

DENTAL IMPRESSION MATERIAL UTILIZING RUTHENIUM METATHESIS CATALYST

CROSS REFERENCE TO RELATED APPLICATION

This application is a continuation-in-part of U.S. patent application Ser. No. 09/690,236 filed Oct. 17, 2000, now patented U.S. Pat. No. 6,455,029 B1 and entitled DENTAL IMPRESSION MATERIAL UTILIZING RUTHENIUM CATALYST, the disclosure of which is incorporated herein by reference in its entirety as if completely set forth herein below.

FIELD OF THE INVENTION

This invention relates to dental impression materials, in particular dental impression materials curable by ring-opening metathesis polymerization with ruthenium complex catalysts.

BACKGROUND OF THE INVENTION

Impression materials used in dentistry are one of several types of elastomers, such as polysulfides, condensation silicones, polyethers or polyvinyl siloxanes (addition-curable silicones). These materials are normally two-paste systems that are mixed immediately before use, then placed in contact with the tooth structure. Mixing of the two pastes initiates a chemical reaction that results in the formation of the elastic rubber impression material after setting, thereby forming a negative impression of the tooth structure involved. The addition-curable silicones, which exhibit fast curing speeds and low shrinkages, typically use a platinum-containing hydrosilation catalyst. This type of catalyst necessitates the use of silicon-containing oligomers, which are generally expensive. Also, the platinum-based catalyst can be inactivated by sulfur-containing impurities present in the latex gloves ordinarily used by dentists, as well as by certain medicaments used in the oral cavity. In addition, there may be undesirable hydrogen evolution from the decomposition of the hydrosiloxane cross-linkers that are present in these systems. This may increase the time and effort necessary to take an impression with these materials because extra precautionary steps have to be taken.

In view of these drawbacks, there is a need for dental impression materials that do not exhibit the various sensitivity problems described above.

SUMMARY OF THE INVENTION

The present invention provides a composition for use as a dental impression material. The composition comprises a polymerizable resin curable by ring-opening metathesis polymerization (ROMP), a dental filler system, and a ruthenium carbene complex catalyst, whereby the catalyst initiates the ring-opening metathesis polymerization of the composition. The polymerizable resin comprises one or more oligomers or polymers that can be tethered and/or end-capped with functional groups such as cycloalkenyl groups that can undergo a metathesis reaction. To phrase it another way, the polymerizable resin may comprise one or a combination of the following: a polymerizable telechelic oligomer or polymer end-capped with a group curable by ROMP; a polymerizable oligomer or polymer tethered and end-capped with a group curable by ROMP, or a polymerizable tri-functional or quadri-functional oligomer or polymer end-capped with a group curable by ROMP. The main chain is advantageously a polydimethylsiloxane.

In an embodiment of the invention, the composition is a base/catalyst system in which the base paste includes the polymerizable oligomer or polymer and an inorganic dental filler system and in which the catalyst paste includes the metathesis catalyst dissolved in an inert solvent and an inorganic dental filler system. In one exemplary embodiment of the present invention, the base paste further includes a silicone-based sulfosuccinate salt, such as dimethicone copolyol sulfosuccinate, for accelerating the catalyst upon mixing of the base paste and catalyst paste. In another exemplary embodiment of the present invention, the oligomer or polymer is a polydimethylsiloxane tethered and end-functionalized with norbornenyl groups and having between 5 and 5000 dimethylsiloxane units, and the catalyst is a ruthenium carbene complex with at least one of the ligands having a basicity higher than tricyclohexylphosphine. The composition of the present invention exhibits reduced sensitivity to sulfur impurities.

DETAILED DESCRIPTION OF THE INVENTION

The present invention provides formulations for dental impression materials using a cyclic olefin containing resin system that is cured by ROMP with the aid of a ruthenium carbene complex metathesis catalyst. Advantageously, the resin system comprises at least one cyclic olefin functionalized oligomer or polymer that is telechelic, tethered, tri-functional or quadri-functional. The resin system may comprise one or a combination of the following: a further polymerizable polymer tethered and end-capped with a group curable by ROMP; a further polymerizable tri-functional oligomer or polymer end-capped with a group curable by ROMP; and a further polymerizable quadri-functional oligomer or polymer end-capped with a group curable by ROMP.

The composition of the present invention advantageously comprises a catalyst paste and base paste in intimate admixture with one another in a paste/paste system. Curing is obtained by a ROMP reaction using a ruthenium carbene as a catalyst. Generally, in this system, the catalyst paste comprises a ruthenium catalyst for initiating polymerization, a solvent for the catalyst that is miscible or dispersible with the base paste, and inorganic fillers for optimizing the viscosity and thixotropy characteristics of the paste for the application and for reinforcement of the cured material. The base paste generally comprises a polymerizable oligomer and/or polymer resin system that is curable via the ROMP mechanism, and inorganic fillers as described above for the catalyst paste. The base paste may further include a silicone-based sulfosuccinate salt, such as a dimethicone copolyol sulfosuccinate compound, for accelerating the catalyst upon mixing of the base paste and catalyst paste, thereby enhancing the efficiency of the catalyst. The base paste may further include a surfactant for providing a water contact angle suitable for dental impression materials.

One type of oligomers and/or polymers that may be used in one embodiment of the present invention include telechelic (end-functionalized/end-capped) polymers with any of a variety of backbones, as long as the chain ends are functionalized with reactive ROMP groups, such as cycloalkenyl groups. For example, the resin may be a telechelic polydimethylsiloxane terminated with norbornenylethyl groups according the following structure:

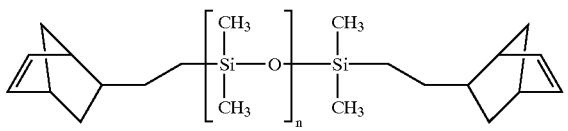

where n=5–5000, for example 27–1590. Other examples of telechelic polysiloxanes are those having the following structure:

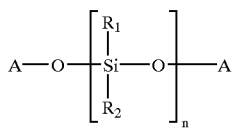

where n=5–5000, such as 27–1590;

$R_1$, $R_2$=$C_1$–$C_{18}$ hydrocarbon or

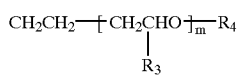

where $R_3$, $R_4$=$C_1$–$C_{18}$ hydrocarbon, and m=0–2; and

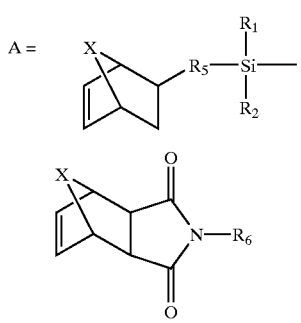

X=$CH_2$, S, O $R_5$=$C_0$–$C_{18}$ hydrocarbon $R_6$=$C_0$–$C_{18}$ hydrocarbon For an alternative example, the resin may be polytetrahydrofuran-polyethylene oxide copolymer terminated with norbornenyl groups. As yet another alternative example, the resin may be a norbornenyl carboxylate terminated polybutadiene.

One type of oligomers and/or polymers that may be used in another embodiment of the present invention include oligomers or polymers tethered and end-capped with groups curable by ROMP, such as cycloalkenyl groups. The oligomers or polymers may have any of a variety of backbones, particularly silicon-containing backbones such as polydimethylsiloxane, with pendant groups incorporated within the backbone or main chain that protrude therefrom thus forming the tethered structure. As with the telechelic polymers, the chain ends are functionalized or capped with reactive ROMP groups, such as cycloalkenyl groups, for example norbornenyl groups. The pendant groups may also be cycloalkenyl groups, such as norbornenyl groups. For example, the resin may be a polydimethylsiloxane tethered and end-capped with norbornenylethyl groups according the following structure:

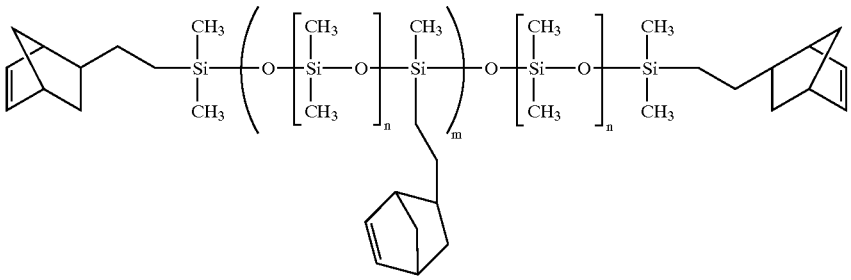

where n=5–5000, for example 27–1590, and m=1–100, for example 1–10.

In yet another embodiment of the present invention, the type of oligomers and/or polymers that may be used include tri- or quadri-functional oligomers or polymers end-functionalized or end-capped with a group curable by ROMP, such as cycloalkenyl groups, for example norbornenyl groups. An example of such polymer is quadri-functional polydimethylsiloxane, end-capped with norbomenylethyl groups.

By way of example, the polymerizable resin may comprise both the telechelic oligomer or polymer and the tethered oligomer or polymer, each end-capped with a group curable by ROMP, or may comprise the telechelic oligomer or polymer and the tethered oligomer or polymer and the quadri-functional oligomer or polymer, each end-capped with a group curable by ROMP. Thus, the resin formulation may be varied to obtain desired physical properties in the uncured and cured dental impression material.

A surfactant may be incorporated into the resin formulation, such as in the base paste, to provide a water contact angle that is suitable for a dental impression material. The inclusion of surfactants, including ionic- and nonionic-type surfactants, is known for imparting hydrophilic properties to hydrophobic substances and for improving the surface wettability. However, the addition of one or more surfactants to the compositions to obtain satisfactory water wettability of the cured composition may result in poor physical properties such as low tensile strength, elongation and tear strength. Nonetheless, the surfactants used can be cationic, anionic, amphoteric or nonionic. A nonionic-type surfactant is preferred, such as one comprising nonylphenoxy poly(ethyleneoxy) ethanol, available from Rhone-Poulenc, Cranbury, N.J., under the trade names IGEPAL® CO-520, CO-530 and the like. Alternatively, a silicone-based surfactant such as Silwet 77 available from Witco Corp., Greenwich, Conn. can be used.

The catalysts useful in the present invention include the ruthenium carbene complexes. The parent benzylidene ruthenium complex A, with the following structure, exhibits high air and water stability:

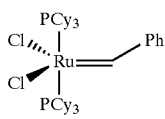

A

The ring-opening metathesis activity of the parent complex A can be increased by substituting a saturated imidazole ligand for a tricyclohexylphosphine ligand. The ligands may be 4,5-dihydroimidazol-2-ylidenes, which have the following general structure:

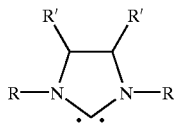

These substituted ligands have a basicity higher than that of tricyclohexylphosphine, as indicated by a higher pKa, which is believed to contribute to the higher activity. Ruthenium complex B, a derivative of complex A and having the structure shown below, is a substituted ruthenium carbene complex including such a ligand:

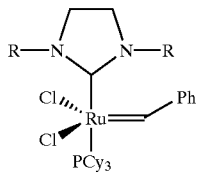

B

Other derivatives of parent complex A can also be used in the resin system of the composition of the present invention, such as substituted ruthenium carbene complexes C and D having the following structures:

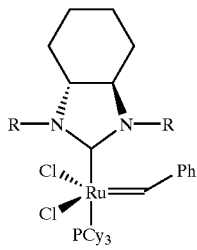

C

-continued

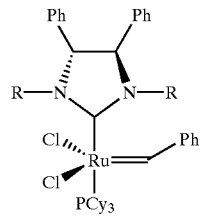

D

The catalyst component of the dental impression material is formulated by dissolving the ruthenium carbene complex in an inert solvent. The solvent, or diluent, is chosen such that the solvent and the complex are miscible (soluble) or dispersible with the base pastes, and such that the solvent does not interfere with the reaction. The solvent may be, for example, 3-phenyl-heptamethyl-trisiloxane. Another exemplary solvent is a partially phenyl substituted poly (dimethylsiloxane), such as Dow Coming fluid 556.

A catalyst accelerator may be incorporated into the resin formulation, such as in the base paste, to further accelerate the ROMP mechanism, thereby enhancing the efficiency of the ruthenium complex catalyst. Silicone-based sulfosuccinate salts act as accelerators for the ruthenium complex catalyst. While dimethicone copolyol sulfosuccinate is normally used as a surfactant for shampoos and the like, as fully described in U.S. Pat. Nos. 4,717,498 and 4,849,127, which are incorporated by reference herein in their entirety, it unexpectedly functions as a catalyst accelerator when used in formulations of the present invention containing the ruthenium complex catalysts. An exemplary accelerator is DC-30A available from McIntyre Chemical Co., Chicago Ill.

The compositions of the present invention also include inorganic dental fillers, and advantageously a mixture of inorganic fillers. Suitable fillers include silicas, aluminas, magnesias, titanium dioxide, zirconium silicate, calcium carbonate, metallic oxides, calcium silicates (Wollastonite), diatomaceous earth and the like. The sizes and surface areas of the fillers are controlled to optimize the viscosity and thixotropy of the resulting suspensions for the dental application. Surface-treated fillers may also be used. Typical surface treatments include silanization and the like. In accordance with the present invention, mixtures of fillers with different particle sizes may be used. A bimodal filler system blended with sub-micron (<1 μm) and micron-sized particles (2–10 μm) of close particle size distribution is used as a varying filler loading to provide dental impression materials with low, medium or high consistency, as defined by ISO Specification No. 4823 (2nd. Ed. 1992), suitable for use in all dental impression techniques. The filler may be present in amounts of from about 15 wt. % to about 70 wt. % of the composition. To adjust the consistency of the two-paste embodiment of the present invention to achieve either a low, medium or high consistency composition, the sub-micron sized filler and/or the micron sized filler may be adjusted in one or both of the catalyst and base pastes. The higher the consistency desired, the more beneficial it is to increase the sub-micron filler to a greater extent than the increase in the micron sized filler, whereby the sub-micron filler particles are worked into the interstitial spaces between micronized particles during mixing.

By way of example only and not limitation, the composition may comprise the polymerizable resin in an amount of about 5 wt. % to about 95 wt. %, the sub-micron sized filler in an amount up to about 10 wt. %, the micron sized filler in an amount of about 10 wt. % to about 70 wt. %, and the catalyst in an amount of about 0.001 wt. % to about 1 wt. %. The composition of the present invention may further include optional additives known to one skilled in the art, such as pigments, that do not interfere with the reaction.

EXAMPLE 1

A telechelic polydimethylsiloxane terminated with norbomenyl ethyl groups (Compound 1) was synthesized according to the following scheme using triethylamine as an acid scavenger:

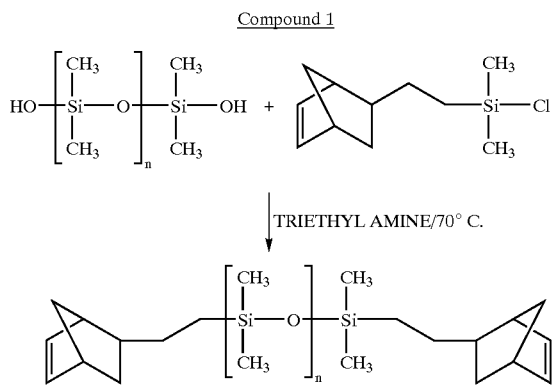

Compound 1

A three-neck round bottom flask equipped with a mechanical stirrer, a condenser and $N_2$ inlet-outlet was charged with 360.0 g silanol terminated poly(dimethylsiloxane) (DMS-S27, n=243, from Gelest Corp.) and 4.85 g triethylamine containing 1% 4-(N,N-dimethyl)amino-pyridine. A quantity of 9.02 g of 2-(5-norbomenyl)ethyl-dimethylchlorosilane (Precursor A) was added dropwise to the flask with stirring. The monochloro-portion of this compound aids in the end-capping process. After the addition, the reaction temperature was raised to 70° C., and stirring was continued for 4 hours at that temperature. Then, 2 mL methanol was added to the mixture and stirring was continued for 1 hour longer. The reaction mixture was next diluted with 500 mL of hexanes and filtered to remove the white salt. The hexane solution was washed three times with 1% HCl and three times with deionized water. The solution was then dried over $Na_2SO_4$. After evaporation of the solvent under vacuum, a clear liquid product was obtained. This Compound 1a, having n=243 (average), exhibited the following infrared peaks ($cm^{-1}$): 2963, 1411, 1260, 1020, 800, and 702.

A second homolog, Compound 1b, was produced following the same procedure as above, but this time using a silanol terminated poly(dimethylsiloxane) having n=27 (average). These two resulting compounds were then mixed and compounded with fillers and dispersed in a three-roll mill to form a suspension. This suspension is referred to as the base component, or base paste, and its composition is detailed in Table 1.

TABLE 1

Test Base Paste Composition

| | |
|---|---|
| Compound 1a, n = 243 | 55.25 wt. % |
| Compound 1b, n = 27 | 9.75 wt. % |

TABLE 1-continued

Test Base Paste Composition

| | |
|---|---|
| Calcium Silicate Wollastonite (2–10 μm average particle size) | 30 wt. % |
| Sub-micron Silica (<1 μm average particle size) | 5 wt. % |
| Total | 100 |

Two catalyst pastes were then formulated by dissolving in 3-phenyl-heptamethyl-trisiloxane the ruthenium carbene complex A and B, respectively, each catalyst complex having been obtained from Strem Chemicals Inc., Newburyport, Mass. The solutions were then compounded with fillers and dispersed in a three-roll mill to form suspensions. These suspensions are referred to as the catalyst components, or catalyst pastes, and are further described in Table 2.

TABLE 2

Test Catalyst Paste Compositions

| | |
|---|---|
| 3-phenyl-heptamethyl-trisiloxane | 64.35 wt. % |
| Calcium Silicate Wollastonite (2–10 μm average particle size) | 30 wt. % |
| Sub-micron Silica (<1 μm average particle size) | 5 wt. % |
| Catalyst A or Catalyst B | 0.65 wt. % |
| Total | 100 |

For comparative purposes, the test base paste composition was combined with each of the test catalyst paste compositions in a base to catalyst ratio of 10:1 and mixed by spatulation. Separately, for use in the comparison, catalyst and base pastes were prepared for an addition-curable silicone composition using a platinum-containing hydrosilation catalyst. The comparative control base paste and control catalyst paste compositions are detailed in Tables 3 and 4, respectively.

TABLE 3

Control Base Paste Composition

| | |
|---|---|
| Polyvinyldimethylsiloxane (4000 cSt.) | 57 wt. % |
| Calcium Silicate Wollastonite (2–10 μm average particle size) | 30 wt. % |
| Sub-micron Silica (<1 μm average particle size) | 5 wt. % |
| Polymethylhydrosiloxane crosslinker (30 cSt.) | 8 wt. % |
| Total | 100 |

TABLE 4

Control Catalyst Paste Composition

| | |
|---|---|
| Polyvinyldimethylsiloxane (4000 cSt.) | 63.5 wt. % |
| Calcium Silicate Wollastonite (2–10 μm average particle size) | 30 wt. % |
| Sub-micron Silica (<1 μm average particle size) | 5 wt. % |
| Platinum Catalyst Complex with Vinylsiloxane | 1.5 wt. % |
| Total | 100 |

The control pastes were combined in a base paste to catalyst paste ratio of 1:1.

Both the test compositions and control compositions are classified as type 2 or 3 impression materials, meaning that they have low to medium consistency, as defined by ISO Specification No. 4823. The physical properties of the cured compositions were determined using ISO Specification No.

4823 for evaluation of work time, set time, mixed consistency, dimensional change, strain and compression and deformation recovery. The results are given below in Table 5.

Table 5 also includes the results of a test devised to determine the relative sensitivity of these formulations to residual sulfur compound containing surfaces, such as latex gloves used by dentists. The sulfur sensitivity test comprised preparing a 1% solution of an approximately 30%/70% mixture of mono- and di-octyl tin bis (2-ethylhexylthioglycolate) esters in hexane. A microbrush was dipped in this solution, and the solution was painted on the edge of a 3×6 inch dental impression mixing pad. The control base paste and the control catalyst paste were mixed in a 1:1 ratio (0.5 g/0.5 g) and the test base paste and the test catalyst paste were mixed in a 10:1 ratio (1.0 g/0.1 g), each by spatulation for 20 seconds, and each mixture was partially placed on top of the area of the pad where the hexane solution was painted on. After the bulk of the material had set, as indicated by set time and recovery from deformation, the mixture was lifted off the pad, and the area that was in contact with the painted area was checked to see if it had also set. The materials were checked 10 minutes after placement on the pad to ascertain whether setting was achieved at the sulfur contact area after the bulk material had already set. The results of this sulfur sensitivity test, along with the physical properties set forth in ISO Specification No. 4823 are set forth in Table 5.

surface within 20 minutes of contacting the sulfur impurity. As defined in ISO specification 4823, a material has set when it develops a recovery from deformation of between 96.5% and 100%. Thus, while the bulk of the impression material may fully set within 10 minutes in each of the test and control materials, surfaces in contact with sulfur impurities may be prevented from setting due to the sulfur deactivating the catalyst, possibly by a chelation mechanism. The parent benzylidene ruthenium complex A caused a reduction in sulfur sensitivity, and the high ring-opening metathesis active ruthenium carbene complexes having substituted imidazole ligands exhibited the highest reduction in sulfur sensitivity during polymerization, as indicated by the full setting of the material at the contacting surface. Thus, compositions of the present invention including a ruthenium carbene complex with a ligand having a basicity higher than that of tricyclohexylphosphine can achieve a recovery after deformation of at least 96.5% within 20 minutes of contacting a thin film of an oxidizable sulfur-containing compound.

The formulations described above contain end-capped oligomers only prepared using triethylamine as the acid scavenger. Although the resultant polymers satisfied the ISO requirements for dental impression materials, their physical property profile as shown by tests on tensile strength, tear strength and elongation (strain to break) was lower than commercial materials. To improve the physical properties, polydimethylsiloxanes end-capped and tethered with nor-

TABLE 5

Physical Properties of Impression Material Pastes

|  | ISO 4823 Specification (Type 2 and 3) | Control | Test 1 | Test 2 |
| --- | --- | --- | --- | --- |
| Catalyst Used |  | Pt Complex | Complex A | Complex B |
| Mixing Ratio (Base:Catalyst) |  | 1:1 | 10:1 | 10:1 |
| Consistency (mm) | ≧36: Type 3 31–39: Type 2 | 34.7 (0.6) | 43 (1) | 33 (2) |
| Work Time (sec.) | >30 | 235 (13) | 198 (10) | 181 (8) |
| Set Time (sec.) |  | 587 (8) | 400 (10) | 327 (12) |
| Strain in Compression (%) | 2–20 | 5.5 (0.2) | 10.7 (0.6) | 6.4 (0.0) |
| Deformation Recovery (%) | 96.5–100 | 99.4 (0.1) | 99.4 (0.1) | 99.8 (0.0) |
| Linear Dimensional Change (after 24 h) (%) | 0–1.5 | 0.06 (0.08) | 0.08 (0.01) | 0.11 (0.02) |
| Detail Reproduction | required | yes | yes | yes |
| Compatibility with Gypsum | required | yes | yes | yes |
| Sulfur Sensitivity |  | No full or partial set in 20 min. | No full set; Partial set after 10 min. | Full set after 10 min. |

From the data in Table 5, it is shown that the materials of the present invention pass the requirements of ISO specification 4823 for Type 2 and/or 3 dental impression materials, including requirements for compatibility with gypsum and detail reproduction.

In addition, the test impression materials exhibited a reduction in sensitivity to sulfur impurities. The test impression material of the present invention incorporating the complex B catalyst exhibited significantly reduced sulfur sensitivity, as indicated by its ability to fully set at surfaces in contact with a sulfur impurity. The test impression material of the present invention utilizing the complex A catalyst at least partially set at the contact surface after 10 minutes, although it did not fully set within 20 minutes after placement. In contrast, the control impression material utilizing the platinum complex catalyst did not set at all at the contact bornenyl groups are incorporated into the formulation for improved strength. Also, potassium hydroxide (KOH) is used as the acid scavenger instead of triethylamine. This simplifies the esterification procedure. The following example illustrates the use of tethered polymers and a KOH acid scavenger.

EXAMPLE 2

Synthesis of the polymer precursor 2-(5-norbornenyl) ethyl methyldichlorosilane (Precursor B) was carried out as follows:

11

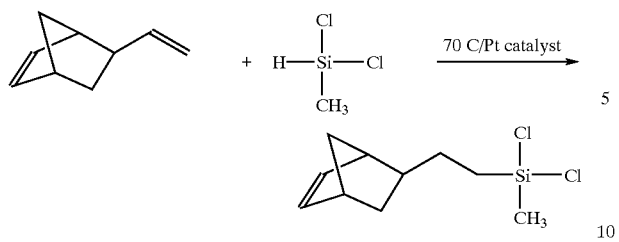

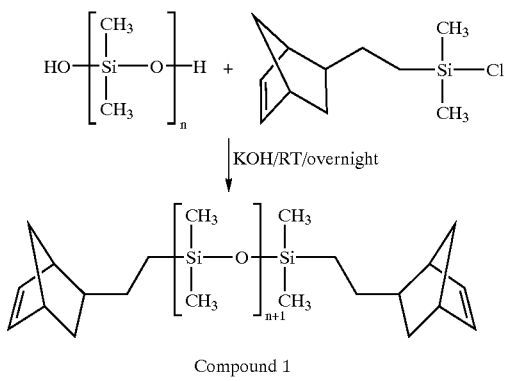

Compound 1

A 500 mL three-neck round bottom flask equipped with a mechanical stirrer, a condenser, $N_2$ inlet-outlet and a dropping funnel was charged with 5-vinyl-2-norbornene (143 mL, 1.0 mol) and platinum catalyst (0.2 g, from Aldrich Chemical, platinum (0) 1,3-divinyl-1,1,3,3-tetramethylsiloxane complex). The temperature of the system was raised to 70° C. Dichloromethylsilane (69 mL, 0.66 mol) was added dropwise. The addition speed was controlled so that the temperature would not exceed 75° C. The reaction was complete in about 3 hours as indicated by the disappearance of Si-H absorption in IR spectrum. Excess 5-vinyl-2-norbornene was removed under vacuum. The Precursor B product was obtained by double vacuum distillation with a boiling point of 65° C. at 0.1 mm. The yield was 68%. Synthesis of Precursor B has been described in LeCamp, L. et al., 33(9) Eur. Polym. J. 1453–1462 (1997).

Synthesis of 2-(5-norbornenyl)ethyldimethylchlorosilane (Precursor A) was carried out using a procedure analogous to that described for Precursor B. The yield was 82%. Synthesis of Precursor A has been described in U.S. Pat. No. 5,266,670, which is incorporated by reference herein in its entirety.

A telechelic poly(dimethylsiloxane) end-capped with norbomenyl groups (Compound 1) was synthesized according to the following scheme using KOH as the acid scavenger:

12

A 500 mL reaction kettle equipped with a mechanical stirrer was charged with 260 g silanol terminated poly (dimethylsiloxane) (PDMS) of 26,000 molecular weight (10 mmol, DMS-S31, n=350 (average), from Gelest Corp.), 1.2 g KOH (22 mmol) and 4.3 g 2-(5-norbornenyl)ethyldimethylchlorosilane (Precursor A) (21 mmol). The mixture was stirred overnight at room temperature (RT). That reaction mixture was diluted with 2 L hexanes and stirred with about 100 g of diatomaceous earth (Celite®, from Spectrum Chemicals). The solution was filtered and solvent was removed on a rotary evaporator to afford Compound 1c, as a clear liquid product having n=350 (average) and a viscosity of 4.9 Pa.s. GPC (toluene) Mn 32,000 and Mw 67,000.

EXAMPLE 3

A poly(dimethylsiloxane) tethered and end-capped with norbomenyl groups (Compound 2) was synthesized according to the following scheme using KOH as acid scavenger:

Compound 2

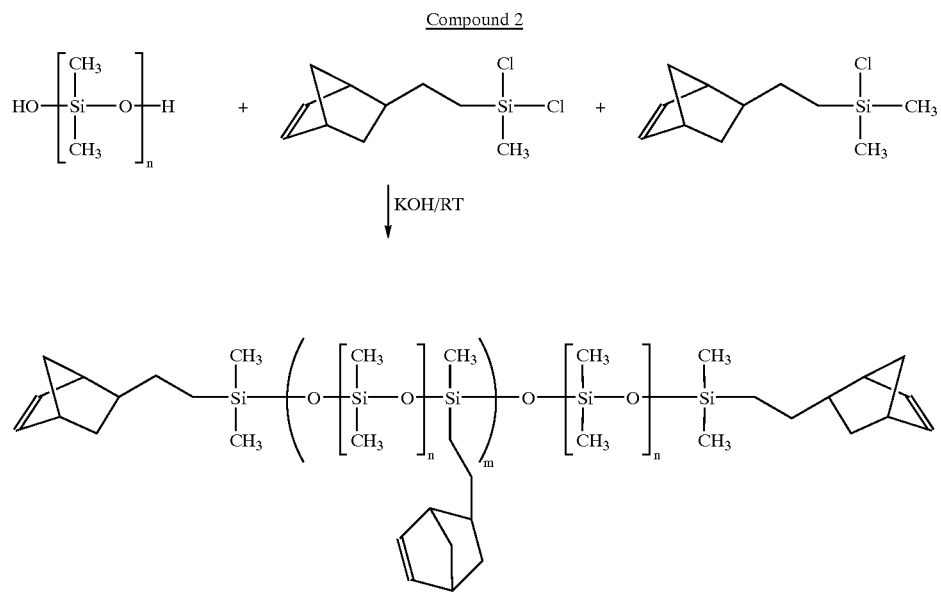

A 500 mL reaction kettle equipped with a mechanical stirrer was charged with 260 g silanol terminated poly (dimethylsiloxane) of 26,000 molecular weight (DMS-S31, n=350 (average), 10 mmol, from Gelest Corp.), 1.23 g KOH (22 mmol), 2.02 g 2-(5-norbornenyl) ethylmethyldichlorosilane (8.56 mmol, Precursor B) and 0.617 g 2-(5-norbornenyl)ethyldimethylchlorosilane (2.87 mmol, Precursor A). Precursor B effects the tethering process, and the Precursor A effects the end-capping process. The mixture was stirred overnight at RT. The viscous resin was diluted with hexanes and stirred with about 100 g diatomaceous earth (Celite®, from Spectrum Chemicals). The solution was then filtered and solvent was removed on a rotary evaporator to afford Compound 2a with a viscosity of 61.6 Pa.s. GPC (toluene) Mn 74,000 and Mw 67,000.

EXAMPLE 4

A quadri-functional poly(dimethylsiloxane), referred to as a Q-resin, end-capped with norbornenyl groups (Compound 3) was synthesized according to the following scheme.

A 500 mL round bottom flask equipped with a Dean-Stark trap and a magnetic spin bar was charged with 300 mL toluene, which was azeotropically refluxed for two hours to remove water. Next, 90 g silanol terminated Q-resin (SQO-299, Mw 3000–4000, OH 1.7–2.0% from Gelest Corp.) was dissolved in the dried toluene. After cooling down, 12.9 g triethylamine (0.13 mol) containing 1% 4-(N, N-dimethyl) aminopyridine (0.13 g, 1.1 mmol) was charged. Then 22.4 g 2-(5-norbornenyl)ethyldimethylchlorosilane (0.104 mol, Precursor A) was added dropwise. The reaction was stirred overnight at RT. The white precipitate was filtered off. The toluene solution was washed three times with 5% HCl (300 mL) and three times with deionized water (300 mL) and dried over $Na_2SO_4$. Evaporation of the solvent on a rotary evaporator afforded a solid product, Compound 3a. The yield was 80%. The results of NMR (Nuclear Magnetic Resonance) analysis is as follows: NMR(1H) 0.15 δ ($CH_3$-Si), 5.9, 6.1 δ (vinyl H).

Low viscosity type 3 impression materials were formulated with the above resins from Examples 2–4 to give handling properties similar to Extrudes, commercially available from Kerr Corp. The base paste formulation is shown below in Table 6:

TABLE 6

Test Base Paste Composition (Wt. %)

| | |
|---|---|
| Base Resin Components | 59.2 |
| Calcium Silicate Wollastonite (2–10 μm average particle size) | 36.8 |
| Sub-micron Silica (2–10 μm average particle size) | 4 |
| Total | 100 |

The compositions of the base resin formulations evaluated are shown below in Table 7:

TABLE 7

Base Resin Composition (Wt. %)

| Base Resin Component | Test 3 | Test 4 | Test 5 | Test 6 | Test 7 |
|---|---|---|---|---|---|
| End-capped PDMS, 1c | 30 | 29.8 | 29.8 | 29.8 | 29.9 |
| Tethered PDMS, 2a | 70 | 70.12 | 69.45 | 59.55 | 69.7 |
| NB functionalized Q-resin, 3a | 0 | 0 | 0 | 9.9 | 0 |
| Accelerator (DC-30A)[1] | 0 | 0.08 | 0.25 | 0.25 | 0.15 |
| Surfactant (Igepal ® CO-520)[2] | 0 | 0 | 0.50 | 0.50 | 0.25 |

[1]A dimethicone copolyol sulfosuccinate ammonium salt available from Mcintyre Chemical Co., Chicago IL.
[2]An ethoxylated alkylphenol available from Rhone-Poulenc, Cranberry NJ.

The catalyst used is 1,3-dimesityl-4,5-dihydroimidazol-2-ylidene-substituted ruthenium carbene complex (B) with the structure indicated above, obtained from Materia Inc., Pasadena, Calif. The catalyst paste was then formulated by dissolving the ruthenium carbene complex B in a partially phenyl substituted poly(dimethylsiloxane), in particular, Dow Coming fluid 556. The solutions were then compounded with inorganic dental fillers and were mixed for 60 seconds in a centrifugal type mixer, (Speed Mix type AM501T, Hauschild Engineering, Hamm, Germany). These suspensions are referred to as the catalyst components, or catalyst pastes, and are further described in Table 8.

TABLE 8

Test Catalyst Paste Composition (Wt. %)

| | |
|---|---|
| Dow Corning Fluid 556 | 39.05 |
| Calcium Silicate Wollastonite (2–10 μm average particle size) | 53.30 |
| Sub-micron Silica (2–10 μm average particle size) | 7.40 |
| Catalyst B | 0.25 |
| Total | 100 |

The curing parameters and some physical properties are given below in Table 9. Two commercially available materials were also tested for comparative purposes, namely Extrude® Type 3 from Kerr Corp. and Imprint® II Type 3 from 3M. These commercial materials include addition-curable silicones crosslinked by a platinum-containing hydrosilation catalyst, in accordance with the prior art and mixed at a 1:1 weight ratio. The test materials 3–7 comprise the catalyst paste of Table 8 and the base paste of Table 6 including the resin components 3–7, respectively, as listed in Table 7. All ROMP cured test materials were mixed in a 10:1 ratio of base paste to catalyst paste. The physical properties of the cured compositions are determined, using ISO Specification No. 4823 for evaluation of work time and set time; and ASTM Standards for the evaluation of tensile strength (ASTM D412, Die D), elongation (ASTM D412, Die D) and tear strength (ASTM 624, Die C). The water contact angle is measured at 60 seconds after a drop of distilled water is applied to a cured composition of the invention, at room temperature using a contact angle goniometer (model 100 made by Rame-Hart, Inc., Mountain Lakes, N.J.).

TABLE 9

Physical Properties of Impression Materials

| Reference | Extrude (Kerr) Type 3 | Imprint II (3M) Type 3 | Test 3 | Test 4 | Test 5 | Test 6 | Test 7 |
|---|---|---|---|---|---|---|---|
| Catalyst Loading (%) | na | na | 0.40 | 0.25 | 0.25 | 0.25 | 0.25 |
| Resin Viscosity, $\eta^*$ at 25° C. (Pa · s) | na | na | 11.63 (0.07) | 10.68 (0.10) | 10.79 (0.11) | 8.88 (0.10) | 11.0 (0.1) |
| Work Time (sec.) | 142 (5) | 192 (2) | 147 | 118 | 112 | 140 | 74 |
| Set Time (sec.) | 246 (8) | 314 (5) | 304 | 272 | 217 | 304 | 187 |
| First Viscosity, $\eta^*$ at 25° C. (Pa · s) on Rheometer (~20 sec.) | 47 (2) | 24 (2) | 49 | 53 | 80 | 57 | 77 |
| Tensile Strength (MPa) (Die D) | 2.24 (0.24) | 1.94 (0.01) | 2.20 (0.31) | 2.23 (0.13) | 1.12 (0.16) | 1.60 (0.11) | 1.44 (0.19) |
| Elongation (%) (Die D) | 220 (28) | 279 (34) | 224 (27) | 320 (14) | 438 (68) | 299 (36) | 423 (106) |
| Shear Strength (N/mm) (Die C) | 5.20 (0.46) | | 4.09 (0.18) | | | | |
| Contact Angle (deg.) | | 36 (1) | 40 (4) | 101 (1) | | 39 (7) | 51 (2) | 58 (1) |

The results show that the ROMP based materials are similar or equivalent to the commercial materials in tensile strength and percent elongation. Test 3 provided acceptable work and set times, viscosities, tensile and tear strengths and percent elongation, but exhibited a high contact angle. Introduction of the surfactant Igepal® CO-520 in the ROMP formulations of tests 5–7 significantly lowered the water contact angle, but led to lower physical properties, in particular tensile strength. Nonetheless, the formulation components can be varied to provide the properties desired in the final uncured paste and cured impression material. It was also observed that the addition of the dimethicone copolyol sulfosuccinate acted as an accelerator for the ruthenium complex catalyst. While dimethicone copolyol sulfosuccinate is normally used as a surfactant for shampoos and the like, as fully described in U.S. Pat. Nos. 4,717,498 and 4,849,127, which are incorporated by reference herein in their entirety, it unexpectedly functions as a catalyst accelerator when used in formulations of the present invention containing the ruthenium complex catalysts, such as catalyst B. As a result, a lesser amount of the catalyst may be used in the formulation, thereby economizing its use. For example, the dental formulation of the present invention may comprise about 0.4–0.5 wt. % catalyst in the absence of the dimethicone copolyol sulfosuccinate, or may comprise about 0.25 wt. % catalyst and about 0.25–0.5 wt. % dimethicone copolyol sulfosuccinate, both formulations having similar physical properties, such as working time.

Additional testing of these types of compounds from McIntyre Chemical Company was performed, specifically, Mackanate DC-30 (Disodium PEG-12 Dimethicone Sulfosuccinate) and Mackanate DC-30A (Diammonium PEG-12 Dimethicone Sulfosuccinate). The first is a marketed product and the second is a developmental product at the present time.

The two dimethicone copolyol sulfosuccinate materials mentioned above were dried to remove water present (approx. 17%) by placing in an oven overnight at 50° C. with 1 mm Hg vacuum. Various amounts of DC-30A were incorporated in formulations very similar to that used in Test 5. The results indicating the variation of working and setting time with increased concentration of DC-30A are shown in Table 10. From these results it appears about 0.25 wt. % is a good level for use in dental impression formulations.

TABLE 10

Working Time Variation with Accelerator Content

| Reference | Test 8 | Test 9 | Test 10 | Test 11 |
|---|---|---|---|---|
| DC-30A dried wt. % | 0 | 0.1 | 0.25 | 0.4 |
| Working Time WT (sec.) | 320 | 147 | 97 | 93 |
| Set Time ST (sec.) | undefined | 496 | 330 | 308 |
| Time to 400 Pa.s (WT) (sec.) | 365 | 134 | 100 | 96 |
| Time to 5000 Pa.s (ST) (sec.) | undefined | 427 | 274 | 259 |

A physical property comparison was done between the two materials. The results are shown in Table 11. Based on the results, DC-30A is a more efficient accelerator, suggesting that ammonium ion plays a key role in the reaction rate change effect.

TABLE 11

Comparison of Efficiency of Accelerators DC-30 and DC-30A

| Reference | Test 3 | Test 12 | Test 13 |
|---|---|---|---|
| Accelerator | None | 0.08% DC-30 dried | 0.08% DC-30A dried |
| Catalyst Loading (%) | 0.40 | 0.25 | 0.25 |
| Resin Viscosity, $\eta^*$ at 25° C. (Pa.s) | 11.63 (0.07) | 11.14 (0.04) | 11.28 (0.11) |
| Working Time WT (sec.) | 147 | 202 | 80 |
| Set Time ST (sec.) | 304 | 660 | 222 |
| Tensile Strength MPa (Die D) | 2.20 (0.31) | 2.18 (0.16) | 1.98 (0.07) |
| Elongation (%) (Die D) | 224 (27) | 252 (12) | 269 (18) |

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative methods and illustrative examples shown and described. Accordingly, departures may be made from such details without departing from the scope or spirit of applicant's general inventive concept.

What is claimed is:

1. A composition for use as a dental impression material, comprising:
   a polymerizable resin comprising at least one oligomer or polymer functionalized with cycloalkenyl groups curable by ring-opening metathesis polymerization and selected from the group consisting of: an oligomer or polymer tethered and end-capped with the groups, a tri-functional oligomer or polymer end-capped with the groups, and a quadri-functional-oligomer or polymer end-capped with the groups;

an inorganic dental filler system; and a ruthenium carbene complex catalyst, wherein the catalyst is capable of initiating the ring-opening metathesis polymerization of the composition to form a cured dental impression material.

2. The composition of claim 1 wherein the polymerizable resin includes polydimethylsiloxane tethered and end-capped with norbornenyl groups and having between about 5 and about 5000 dimethylsiloxane units.

3. The composition of claim 2 wherein the polydimethylsiloxane includes between about 27 and about 1590 dimethylsiloxane units.

4. The composition of claim 1 wherein the composition comprises about 5 wt. % to about 95 wt. % of the polymerizable resin.

5. The composition of claim 1 wherein the filler system is bimodal, including a sub-micron sized filler component and a micron sized filler component.

6. The composition of claim 5 wherein the composition comprises up to about 10 wt % sub-micron sized filler and about 10 wt % to about 70 wt. % micron sized filler.

7. The composition of claim 1 wherein the catalyst is a benzylidene ruthenium complex of the formula:

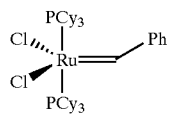

A wherein Cy is cyclohexyl and Ph is phenyl.

8. The composition of claim 1 wherein the catalyst is a 4,5-dihydroimidazol-2-ylidene-substituted ruthenium carbene complex.

9. The composition of claim 1 wherein the catalyst is a ruthenium carbene complex with one ligand having a basicity higher than tricyclohexylphosphine.

10. The composition of claim 9 wherein the complex is of the formula:

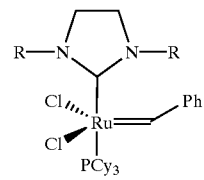

B wherein Cy is cyclohexyl, Ph is phenyl and R is mesityl.

11. The composition of claim 9 wherein the complex is of the formula:

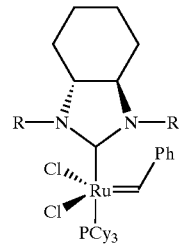

C wherein Cy is cyclohexyl, Ph is phenyl and R is mesityl.

12. The composition of claim 9 wherein the complex is of the formula:

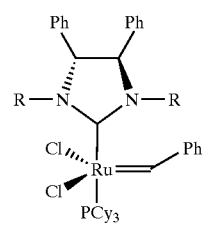

D wherein Cy is cyclohexyl, Ph is phenyl and R is mesityl.

13. The composition of claim 1 wherein the composition achieves a recovery after deformation of at least 96.5% within 20 minutes of contacting a film of an oxidizable sulfur-containing compound.

14. The composition of claim 1 wherein the composition comprises about 0.001 wt. % to about 1 wt. % of the catalyst.

15. The composition of claim 1 wherein the group is a norbornenyl group.

16. The composition of claim 1 wherein the polymerizable resin is polydimethylsiloxane tethered and end-capped with norbornenyl groups and having the formula:

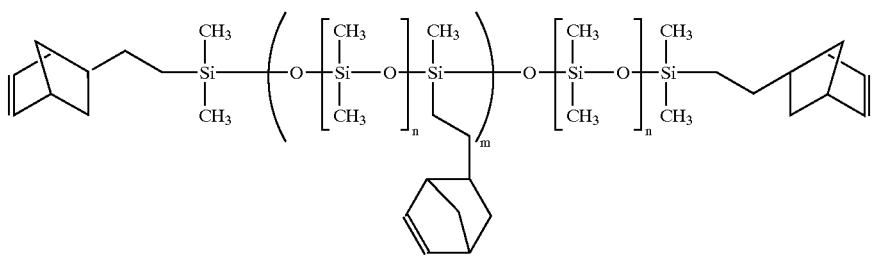

where n=5–5000, and m=1–100.

17. The composition of claim 1 wherein the polymerizable resin includes polydimethylsiloxane tethered and end-capped wit cycloalkenyl groups.

18. The composition of claim 1 further comprising a silicone-based sulfosuccinate compound for accelerating the catalyst.

19. The composition of claim 1 further comprising a dimethicone copolyol sulfosuccinate ammonium salt for accelerating the catalyst.

20. The composition of claim 1 further comprising an ethoxylated alkylphenol surfactant.

21. The composition of claim 1 wherein the polymerizable resin includes norbornenyl functionalized quadri-functional polydimethylsiloxane.

22. The composition of claim 1 wherein the polymerizable resin includes telechelic polydimethylsiloxane end-functionalized with norbomenyl groups and polydimethylsiloxane tethered and end-functionalized with norbornenyl groups.

23. The composition of claim 22 wherein the polymerizable resin further includes quadri-functional polydimethylsiloxane end-functionalized with norbornenyl groups.

24. A composition for use as a dental impression material, comprising:
   a base paste including a polymerizable resin comprising at least one polydimethylsiloxane functionalized with cycloalkenyl groups curable by ring-opening metathesis polymerization and selected from the group consisting of: polydimethylsiloxane tethered and end-capped with the groups, tri-functional polydimethylsiloxane end-capped with the groups, and quadri-functional polydimethylsiloxane end-capped with the groups, and an inorganic dental filler system; and
   a catalyst paste including a ruthenium carbene complex catalyst dissolved in a solvent which is miscible wit the base paste and an inorganic dental filler system, wherein the catalyst is capable of initiating the ring-opening metathesis polymerization of the composition to form a cured dental impression material.

25. The composition of claim 24, herein the ratio of the base paste to the catalyst paste in the composition is in the range of about 10:1 to about 1:1.

26. The composition of claim 24, wherein the polymerizable resin further includes a telechelic polydimethylsiloxane end-capped wit a group curable by ring-opening metathesis polymerization.

27. The composition of claim 14 wherein the group is a norbornenyl group and the polydimethylsiloxane has between about 5 and about 5000 dimethylsiloxane units.

28. The composition of claim 27, wherein the polydimethylsiloxane includes between about 27 and about 1590 dimethylsiloxane units.

29. The composition of claim 24 wherein the composition comprises about 5 wt. % to about 95 wt. % of the polymerizable resin.

30. The composition of claim 24 wherein the filler system in each of The base paste and the catalyst paste is bimodal, including a sub-micron sized filler component and a micron sized filler component.

31. The composition of claim 30 wherein the composition comprises up to about 10 wt. % sub-micron sized filler and about 10 wt. % to about 60 wt. % micron sized filler.

32. The composition of claim 24 wherein the catalyst is a benzylidene ruthenium complex of the formula:

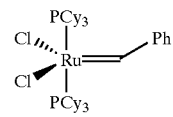

wherein Cy is cyclohexyl and Ph is phenyl.

33. The composition of claim 24 wherein the catalyst is a 4,5-dihydroimidazol-2-ylidene-substituted ruthenium carbene complex.

34. The composition of claim 24 wherein the catalyst is a ruthenium carbene complex with one ligand having a basicity higher than tricyclohexylphosphine.

35. The composition of claim 34 wherein the complex is of the formula:

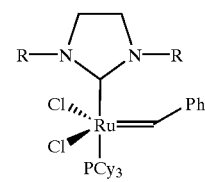

wherein Cy is cyclohexyl, Ph is phenyl and R is mesityl.

36. The composition of claim 34 wherein the complex is of the formula:

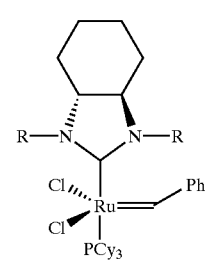

wherein Cy is cyclohexyl, Ph is phenyl and R is mesityl.

37. The composition of claim 34 wherein the complex is of the formula:

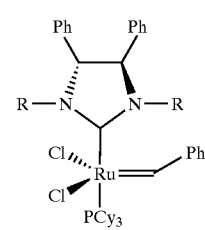

wherein Cy is cyclohexyl, Ph is phenyl and R is mesityl.

38. The composition of claim 24 wherein the composition achieves a recovery after deformation of at least 96.5% within 20 minutes of contacting a film of an oxidizable sulfur-containing compound.

39. The composition of claim 24 wherein the composition comprises about 0.001 wt. % to about 1 wt. % of the catalyst.

40. The composition of claim 24 wherein the group is a norbomenyl group.

41. The composition of claim 24 wherein the polymerizable resin includes polydimethylsiloxane tethered and end-capped wit norbornenyl groups and having the formula:

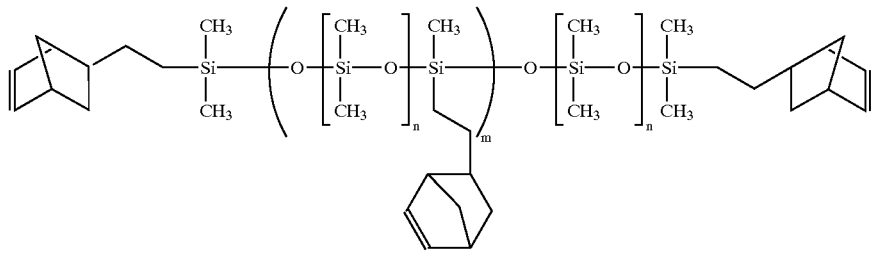

where n=5–5000, and m=1–100.

42. The composition of claim 24 wherein the polymerizable resin includes polydimethylsiloxane tethered and end-capped with cycloalkenyl groups.

43. The composition of claim 24 further comprising a silicone-based sulfosuccinate compound for accelerating the catalyst.

44. The composition of claim 24 further comprising a dimethicone copolyol sulfosuccinate ammonium salt for accelerating the catalyst.

45. The composition of claim 24 further comprising an ethoxylated alkylphenol surfactant.

46. The composition of claim 24 wherein the polymerizable resin includes norbornenyl functionalized quadri-functional polydimethylsiloxane.

47. The composition of claim 24 wherein the polymerizable resin includes telechelic polydimethylsiloxane end-functionalized with norbornenyl groups and polydimethylsiloxane tethered and end-functionalized with norbornenyl groups.

48. The composition of claim 47 wherein the polymerizable resin further includes quadri-functional polydimethylsiloxane end-functionalized with norbornenyl groups.

49. A composition for use as a dental impression material, comprising:

a base paste including a polymerizable resin comprising at least one polydimethylsiloxane functionalized wit cycloalkenyl groups curable by ring-opening metathesis polymerization and selected from the group consisting of: polydimethylsiloxane tethered and end-capped with the groups, td-functional polydimethylsiloxane end-capped wit the groups, and quadri-functional polydimethylsiloxane end-capped with the groups, and an inorganic dental filler system; and a catalyst paste including a substituted ruthenium carbene complex with a substituted ligand having a basicity higher than tricyclohexylphosphine, the complex dissolved in a solvent which is miscible with the base paste, and an inorganic dental filler system, wherein the catalyst is capable of initiating the ring-opening metathesis polymerization of the composition, and wherein the composition achieves a recovery after deformation of at least 96.5% within 20 minutes of contacting a solution of 1% or less of an oxidizable sulfur-containing compound in hexane.

50. The composition of claim 48 wherein the polymerizable resin includes polydimethylsiloxane tethered and end-capped with cycloalkenyl groups.

51. The composition of claim 48 wherein the base paste further comprises a silicone-based sulfosuccinate compound for accelerating the catalyst.

52. The composition of claim 48 wherein the base paste further comprises a dimethicone copolyol sulfosuccinate ammonium salt for accelerating the catalyst.

53. The composition of claim 48 wherein the base paste further comprises an ethoxylated alkylphenol surfactant.

54. The composition of claim 48 wherein the polymerizable resin includes norbornenyl functionalized quadri-functional polydimethylsiloxane.

55. The composition of claim 48 wherein the polymerizable resin includes telechelic end-functionalized with norbornenyl groups and polydimethylsiloxane tethered and end-functionalized with norbornenyl groups.

56. The composition of claim 55 wherein the polymerizable resin further includes quadri-functional polydimethylsiloxane end-functionalized with norbornenyl groups.

* * * * *

UNITED STATES PATENT AND TRADEMARK OFFICE
CERTIFICATE OF CORRECTION

PATENT NO.     : 6,649,146 B2
DATED          : November 18, 2003
INVENTOR(S)    : Angeletakis et al.

It is certified that error appears in the above-identified patent and that said Letters Patent is hereby corrected as shown below:

Title page,
Item [56], References Cited, U.S. PATENT DOCUMENTS, should include the following:

| | | | |
|---|---|---|---|
| --4,717,498 | 1/1988 | Maxon | 252/174.15 |
| 4,849,127 | 7/1989 | Maxon | 252/174.15 |
| 5,266,670 A | 11/1993 | Nakos et al. | 252/174.15 |
| 5,728,785 A | 3/1998 | Grubbs et al. | 252/174.15 |
| 6,075,068 A | 6/2000 | Bissinger | 252/174.15-- |

FOREIGN PATENT DOCUMENTS, should include the following:

-- EP 1025830      8/2000 . . . . . . . . . . . . A61K/6/087 --

OTHER PUBLICATIONS, should include the following:

--International Organization for Standardization, Dental Elastomeric Impression Materials, ISO 4823 (1992).
Scholl et al., Synthesis and Activity of a New Generation of Ruthenium-Based Olefin Metathesis Catalysts Coordinated with 1,3-Dimesityl-4,5-dihydroimidazol-2-ylidene Ligands, Org. Lett., Vol. 1, No. 6, 953-956 (1999).
Chevalier et al., Ring-Opening Olefin Metathesis Polymerisation (ROMP) as a Potential Cross-Linking Mechanism for Siloxane Polymers, J. of Inorganic and Organometallic Polymers, Vol. 9, No. 3, 151-164 (1999).
L. LeCamp et al., Polydimethyl Siloxane Photoreticulable par Voie Cationique-1, Eur. Polym. J. Vol. 33, No. 9, pp. 1453-1462 (1997).--

Column 4,
Line 3, "norbomenyl" should be -- norbornenyl --.
Lines 46-47, "norbormenyl" should be -- norbornenyl --.
Lines 48-49, "norbomenylethyl" should be -- norbornenylethyl --.

Column 7,
Lines 9-10, "norbomenyl" should be -- norbornenyl --.
Line 36, "norbomenyl" should be -- norbornenyl --.
Line 49, "la" should be -- 1a --.

UNITED STATES PATENT AND TRADEMARK OFFICE
CERTIFICATE OF CORRECTION

PATENT NO.    : 6,649,146 B2
DATED         : November 18, 2003
INVENTOR(S)   : Angeletakis et al.

It is certified that error appears in the above-identified patent and that said Letters Patent is hereby corrected as shown below:

Column 10,
Lines 53 and 65, "norbomenyl" should be -- norbornenyl --.

Column 11,
Lines 15, 24 and 29, "norbomene" should be -- norbornene --.
Lines 36-37, "norbomenyl" should be -- norbornenyl --.

Column 12,
Line 37, "norbomenyl" should be -- norbornenyl --.

Column 13,
Line 50, "Extrudes" should be -- Extrude® --.

Column 14,
Line 27, "Dow Coming" should be -- Dow Corning --.
Line 12, "Shear Strength" should be -- Tear Strength --.

Column 17,
Line 4, "quadri-functional-oligomer" should be -- quadri-functional oligomer --.

Column 19,
Line 4, "wit" should be -- with --.
Line 19, "norbomenyl" should be -- norbornenyl --.
Lines 38 and 48, "wit" should be -- with --.
Line 50, "claim 14" should be -- claim 24 --.
Line 60, "of The base paste" should be -- of the base paste --.

Column 20,
Line 64, "norbomenyl" should be -- norbornenyl --.
Line 67, "wit" should be -- with --.

Column 21,
Lines 40 and 45, "wit" should be -- with --.
Line 44, "td-functional" should be -- tri-functional --.

UNITED STATES PATENT AND TRADEMARK OFFICE
CERTIFICATE OF CORRECTION

PATENT NO. : 6,649,146 B2
DATED : November 18, 2003
INVENTOR(S) : Angeletakis et al.

It is certified that error appears in the above-identified patent and that said Letters Patent is hereby corrected as shown below:

Column 22,
Lines 26, 29, 32, 35, 37 and 40, "claim 48" should be -- claim 49 --.
Line 41, "telechelic end-functionalized" should be -- telechelic polydimethylsiloxane end-functionalized --.

Signed and Sealed this

Thirteenth Day of April, 2004

JON W. DUDAS
*Acting Director of the United States Patent and Trademark Office*